United States Patent [19]
Feuerstein et al.

[11] Patent Number: 6,096,777
[45] Date of Patent: Aug. 1, 2000

[54] METHOD FOR INHIBITING THE EXPRESSION OF FAS

[75] Inventors: Giora Zeev Feuerstein, Wynnewood; Tian-Li Yue, Havertown, both of Pa.

[73] Assignees: Boehringer Mannheim Pharmaceuticals Corporation; SmithKline Bechman Corporation Limited Partnership No. 1, both of Gaithersburg, Md.

[21] Appl. No.: 09/242,595

[22] PCT Filed: Aug. 22, 1997

[86] PCT No.: PCT/US97/14792

§ 371 Date: Feb. 22, 1999

§ 102(e) Date: Feb. 22, 1999

[87] PCT Pub. No.: WO98/07321

PCT Pub. Date: Feb. 26, 1998

Related U.S. Application Data

[60] Provisional application No. 60/024,486, Aug. 23, 1996.

[51] Int. Cl.$^7$ .................................................. A61K 31/40
[52] U.S. Cl. .............................................................. 514/411
[58] Field of Search ............................................. 514/411

[56] References Cited

U.S. PATENT DOCUMENTS 4,503,067  3/1985  Wiedemann et al. .

OTHER PUBLICATIONS

J. of Cardiovascular Pharm; Senior, et al., "Effects of Carvedilol on Ventricular Arrhythmias", 1992, vol. 19, (Suppl. 1): pp. S117–S121.
J. of Cardiovascular Pharm; DasGupta, et al., "The Effects of Intravenous Carvedilol, A New Multiple Action Vasodilatory β–Blocker, in Congestive Heart Failure", 1991, vol. 18, (Suppl. 1): pp. S12–S16.
Vacek, et al., Vnitr. Lek., 1994, vol. 40, No. 4, Doc. No. 124:250307.
Feuerstein, et al., Drugs Today, 1995, vol. 31, Suppl. F, Doc. No. 124:75193.
American J. of Cardiology; DasGupta, et al., "Value of Carvedilol in Congestive Heart Failure Secondary to Coronary Artery Disease", 1990, vol. 66, pp. 1118–1123.
Z. Kardiol; A. Buchwald, et al., "Acute Hemodynamic Effects of the Beta–blocker Carvedilol in Heart Failure", 1990, vol. 79, No. 6, pp. 424–428.
JACC; DiLenarda, et al., "Acute Hemodynamic Effects of Carvedilol Versus Metoprolol In Idiopathic Dilated Cardiomyopathy", 1991, vol. 17, No. 2, Absrtact 142A.
Frontiers in CHF;D. Tepper, "Multicenter Oral Carvedilol Heart Failure Assesments", 1996, vol. 2, No. 1, pp. 39–40.
J. of Cardiovascular Pharm; DasGupta, et al., 1990, vol. 19, (Suppl. 1): pp. 562–567.
J. of Hypertension; C. Rosendorff, "Beta–blocking agents with vasodilator activity", 1993, vol. 11, (Suppl. 4): pp. S37–S40.
Cardiology; J. Lessem, et al., "Development of a Multi-action Beta–blocker", 1993, vol. 82, (Suppl. 3): pp. 50–58.
Drug Safety; W.J. Louis, et al., "A Risk–Benefit Assessment of Carvedilol in the Treatment of Cardiovascular Disorders", 1994, vol. 11, No. 2, pp. 86–93.
Drugs; McTavish, et al., "Carvedilol—A Review of its Pharmacodynamic and Pharmacokinetic Properties, and Therepeutic Efficacy", 1993, vol. 45, No. 2, pp. 232–258.
Circulation; H. Krum, et al., "Effects of Carvedilol, a Vasodilator–β–Blocker, in Patients with Congestive Heart Failure Due to Ischemic Heart Disease", 1995, vol. 92, No. 2, pp. 212–218.
CBS–TV; CBS Evening News, Transcript, Jan. 27, 1993, 6:30–7:00pm.
CNBC; Steals and Deals, Transcript, Jan. 29, 1993, 8:30pm.
Circulation; DasGupta, et al., 1989, vol. 80, No. 4, (Suppl. II): pp. 116–117.
Drugs to Today; Ruffolo, et al., "Carvedilol(Kredex ): A Novel Multiple Action Cardiovascular Agent", 1991, vol. 27, No. 7, pp. 465–492.
Cardiovascular Drug Review; Ruffolo, et al., Carvedilol: "A Novel Cardiovascular Drug with Multiple Actions", 1992, vol. 10, No. 2, pp. 127–157.

*Primary Examiner*—Raymond Henley, III
*Attorney, Agent, or Firm*—Mary E. McCarthy; Stephen Venetianer; Charles M. Kinzig

[57] ABSTRACT

The present invention relates to a new method of treatment using compounds which are dual non-selective beta-adrenoceptor and alpha-1-adrenoceptor antagonists, in particularly the carbazolyl-(4)-oxypropanolainine compounds of Formula 1, as defined herein, for inhibiting the expression of Fas, a cell surface protein.

20 Claims, No Drawings

METHOD FOR INHIBITING THE EXPRESSION OF FAS

This application claim priority from U.S. Provisional Application 60/024,486 filed Aug. 23, 1996 and is a 371 of PCT/US97/14792 filed Aug. 22, 1997.

FIELD OF THE INVENTION

The present invention relates to a new method of treatment using compounds which are dual non-selective β-adrenoceptor and $α_1$-adrenoceptor antagonists, in particular the carbazolyl-(4)-oxypropanolamine compounds of Formula I, preferably carvedilol, for inhibiting the expression of Fas, a cell surface protein.

BACKGROUND OF THE INVENTION

Cell proliferation, differentiation, and survival are often regulated by growth, differentiation, and survival factors, respectively, which are collectively called cytokines. Cytokines bind to their complementary receptors, which transduce the extracellular signal into an intracellular signaling cascade. Fas ligand (FasL) is a cytokine. It is one of the few known cytokines that is a death factor. This ligand binds to its receptor, Fas, a cell-surface protein, and induces apoptosis (cell death). Many tissues and cell lines weakly express Fas, but abundant expression has been found in mouse heart, liver, lung, kidney, ovary and thymus (R. Watanabe-Fukunaga, et al., *J. Immunol.*, 148, 1274–1279 (1992)). In the immune system, Fas and FasL are involved in down-regulation of immune reactions as well as in T cell-mediated cytotoxicity. Malfunction of the Fas system causes lymphoproliferative disorders and accelerates autoimmune diseases, whereas its exacerbation may cause tissue destruction (S. Nagata, et al., *Science*, 267, 1449–1456 (1995)).

Surprisingly, it has been found that carvedilol, a dual non-selective β-adrenoceptor and $α_1$-adrenoceptor antagonist, inhibits the expression of Fas. This inhibition may mean that carvedilol and related Formula I compounds are useful for diseases wherein inhibition of Fas-mediated apoptosis is indicated. Particularly, this inhibition may mean that carvedilol and related Formula I compounds are useful for blocking ischemia-induced apoptosis in cardiac cells, for preventing or inhibiting tissue remodeling, in particular in cardiac tissue and blood vessels, for treating autoimmune diseases, and for inhibiting tumor growth and metastasis.

SUMMARY OF THE INVENTION

The present invention relates to a new method of treatment using compounds which are dual non-selective β-adrenoceptor and $α_1$-adrenoceptor antagonists, in particular the carbazoiyl-(4)-oxypropanolamine compounds of Formula I, preferably carvedilol, for inhibiting the expression of Fas. The invention also relates to a method of treatment using compounds which are dual non-selective β-adrenoceptor and $α_1$-adrenoceptor antagonists, in particular the carbazolyl-(4)-oxypropanolamine compounds of Formula I, preferably carvedilol, for inhibiting apoptosis. Furthermore, this invention relates to a method of treatment using compounds which are dual non-selective β-adrenoceptor and $α_1$-adrenoceptor antagonists, in particular the carbazolyl-(4)-oxypropanolamine compounds of Formula I, preferably carvedilol, for diseases wherein inhibition of Fas-mediated apoptosis is indicated. In particular, this invention is directed to the use of Formula I compounds, preferably carvedilol, to specifically induce Fas-mediated apoptosis of undesirable cells, such as cancer or autoreactive immune cells. Additionally, when control of aberrant forms of Fas activation is desired, the Formula I compounds, preferably carvedilol, are used to prevent cell depletion in AIDS or neurodegenerative diseases.

This invention also relates to a method of treatment using compounds which are dual non-selective β-adrenoceptor and $α_1$-adrenoceptor antagonists, in particular the carbazolyl-(4)-oxypropanolamine compounds of Formula I, preferably carvedilol, for preventing or inhibiting tissue remodeling, in particular in cardiac tissue and blood vessels. The present method includes the use of compounds which are dual non-selective β-adrenoceptor and $α_1$-adrenoceptor antagonists, in particular the carbazolyl-(4)-oxypropanolarnine compounds of Formula I, preferably carvedilol, to block ischemia-induced apoptosis in cardiac cells.

DETAILED DESCRIPTION OF THE INVENTION

The present invention provides a new method for inhibiting the expression of Fas using compounds which are dual non-selective β-adrenoceptor and $α_1$-adrenoceptor antagonists. Preferably, this invention provides a new method for inhibiting the expression of Fas using compounds of Formula I:

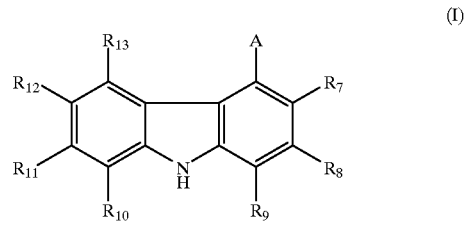

wherein:

$R_7$–$R_{13}$ are independently —H or —OH; and

A is a moiety of Formula II:

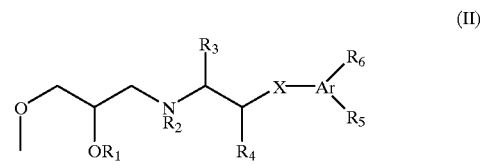

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a single bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy; and pharmaceutically acceptable salts thereof.

More preferably, the present invention provides a new method for inhibiting the expression of Fas using compounds of Formula III:

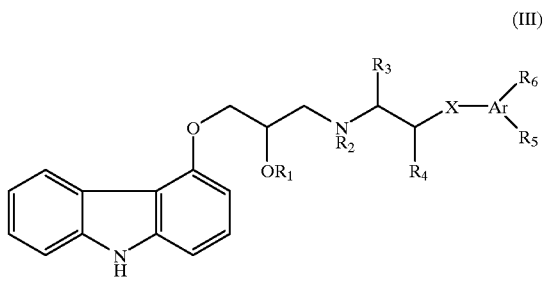

(III)

wherein:
$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a single bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsuiphonyl of up to 6 carbon atoms; or $R_5$ and $R_6$ together represent methylenedioxy; and pharmaceutically acceptable salts thereof.

Most preferably, the present invention provides a new method for inhibiting the expression of Fas using a compound of Formula IV, better known as carvedilol or (1-(carbazol-4-yloxy-3-[[2-(o-methoxyphenoxy)ethyl]amino]-2-propanol):

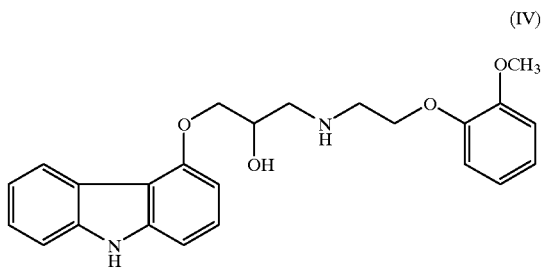

(IV)

The compounds of the present invention are novel multiple action drugs useful in the treatment of mild to moderate hypertension. Carvedilol is known to be both a competitive non-selective β-adrenoceptor antagonist and a vasodilator, and is also a calcium channel antagonist at higher concentrations. The vasodilatory actions of carvedilol result primarily from $\alpha_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans. See Willette, R. N., Sauermelch, C. F. & Ruffolo, R. R., Jr. (1990) *Eur. J. Phannacol.*, 176,237–240; Nichols, A. J., Gellai, M. & Ruffolo, R. R., Jr. (1991) *Fundam. Clin. Phannacol.*, 5, 25–38; Ruffolo, R. R., Jr., Gellai, M., Hieble, J. P., Willette, R. N. & Nichols, A. J. (1990) *Eur. J. Clin. Pharmacol.*, 38, S82–S88; Ruffolo, R. R., Jr. Boyle, D. A., Venuti, R. P. & Lukas, M. A. (1991) *Drugs of Today*, 27, 465–492; and Yue, T.-L., Cheng, H., Lysko, P. G., Mckenna, P. J., Feuerstein, R., Gu, J., Lysko, K. A., Davis, L. L. & Feuerstein, G. (1992) *J. Pharmacol. Exp. Ther.*, 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble. J. P., Willette, R. N. & Nichols, A. J. (1990) *Eur. J. Clin. Pharmacol.*, 38, S82–S88. Carvedilol also markedly reduces infarct size in rat, canine and porcine models of acute myocardial infarction, Ruffolo, R. R., Jr., et al., *Drugs of Today*, supra, possibly as a consequence of its antioxidant action in attenuating oxygen free radical-initiated lipid peroxidation. Yue, T.-L., et al. supra.

Recently, it has been discovered that compounds which are dual non-selective β-adrenoceptor and $\alpha_1$-adrenoceptor antagonists, in particular the compounds of Formula I, preferably carvedilol, inhibit the expression of Fas and inhibit Fas-mediated apoptosis. Based on this mechanism of action, the instant compounds can be used to treat diseases wherein inhibition or control of Fas-mediated apoptosis is indicated. In particular, the compounds of the current invention, preferably carvedilol, can be used for blocking ischermia-induced apoptosis in cardiac cells, for preventing or inhibiting tissue remodeling, in particular in cardiac tissue and blood vessels, for treating autoimmune diseases, and for inhibiting tumor growth and metastasis. Additionally, when control of aberrant forms of Fas activation is desired, the Formula I compounds, preferably carvedilol, are used to prevent cell depletion in AIDS or neurodegenerative diseases.

Some of the compounds of Formula I are known to be metabolites of carvedilol. Certain preferred compounds of the present invention, that is, the compounds of Formula I wherein A is the moiety of Formula II wherein R1 is —H. R2 is —H. R3 is —H, R4 is —H, X is O, Ar is phenyl, R5 is ortho —OH, and R6 is —H, and one of $R_7$, $R_9$, or $R_{10}$ is —OH, are metabolites of carvedilol.

Compounds of Formula I may be conveniently prepared as described in U.S. Pat. No. 4,503,067. Reference should be made to said patent for its full disclosure, the entire disclosure of which is incorporated herein by reference.

Pharmaceutical compositions of the compounds of Formula I, including carvedilol, may be administered to patients according to the present invention in any medically acceptable manner, preferably orally. For parenteral administration the pharmaceutical composition will be in the form of a sterile injectable liquid stored in a suitable container such as an ampoule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula I for use according to the present invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed a dosage range of from about 3.125 to about 50 mg of the compounds of Formula I, particularly carvedilol, preferably given twice daily. As one of ordinary skill in the art will readily comprehend, the patient should be started on a low dosage regimen of the desired compound of Formula I, particularly carvedilol, and monitered for well-known symptoms of intolerance, e.g., fainting, to such compound. Once the patient is found to tolerate such compound, the patient should be brought slowly and incrementally up to the maintenance dose. The choice of initial dosage most appropriate for the particular patient is determined by the practitioner using well-known medical principles, including, but not limited to, body weight. In the event that the patient exhibits medically acceptable tolerance of the compound for two weeks, the dosage is doubled at the end of the two weeks and the patient is maintained at the new, higher dosage for two more weeks, and observed for signs of intolerance. This course is continued until the patient is brought to a maintenance dose.

It will be appreciated that the actual preferred dosages of the compounds being used in the compositions of this invention will vary according to the particular composition formulated, the mode of administration, the particular site of administration and the host being treated.

No unacceptable toxicological effects are expected when the compounds of Formula I are used according to the present invention.

The example which follows is intended in no way to limit the scope of this invention, but is provided to illustrate how to use the compounds of this invention. Many other embodiments will be readily apparent to those skilled in the art.

EXPERIMENTAL

The effect of carvedilol on myocardial apoptosis was investigated in a rabbit model of cardiac ischemia and reperfusion (R. Gottlieb, et al., *J. Clin. Invest.*, 94, 1621–1628 (1994)). In this model, ischemia and reperfusion elicits widespread apoptosis in cardiac myocytes. Carvedilol treatment prior to the ischemic insult significantly reduced the apoptotic myocytes from 14.7 cells per field to 4.5 cells per field ($p<0.01$).

Immunochemical Detection of Fas Expression of Rabbit Cardiomyocytes

Heart tissue was fixed in NBF for 24–48 hr at 4° C. and cut longitudinally into 2–3 mm-thick piece. Following standard histological processing and embedding in paraffin, 5 $\mu$m-thick sections were prepared for immunoperoxidase staining using the Vectastain ABC kit (Vector Laboratories) according to the manufacturer's instructions. Briefly, endogenous peroxidase was quenched with 0.3% $H_2O_2$ in methanol for 30 minutes. Nonspecific immunoglobulin binding sites were blocked with normal goat serum for 1 hour and then the sections were incubated with the primary antibody (mouse anti-FAS, 2 $\mu$g/ml, Upstate Biotechnology) for 1 hour at room temperature. The sections were then incubated for 30 minutes with a biotinylated goat anti-mouse IgM secondary antibody (1:200, Vector Laboratories) followed by 30 minutes of incubation with the Vectastain ABC reagent solution. Immunogiobulin complexes were visualized upon incubation with 3,3'-diaminobenzidine (DAB, Vector Laboratories) at 0.5 mg/ml in 50 mM Tris-HCl, pH 7.4 and 3% $H_2O_2$. DAB staining was enhanced by treating the sections for 10 seconds with DAB Enhancing Solution (Vector Laboratories). Sections were washed, counterstained with Gill's Hematoxylin, cleared, mounted with Aquamount (Polysciences), and then examined by light microscopy.

In summary, comparative studies were conducted wherein basil levels of Fas was expressed in normal heart cardiomyocytes. In ischemic reperfusion injury, the expression of Fas in cardiomyocytes was stimulated. With carvedilol treatment, this reperfusion-induced expression of Fas in cardiomyocytes was inhibited.

The foregoing is illustrative of the use of the compounds of this invention. This invention, however, is not limited to the precise embodiment described herein, but encompasses all modifications within the scope of the claims which follow.

What is claimed is:

1. A method for inhibiting the expression of Fas which comprises administering to a mammal in need thereof an effective amount of a compound which is a dual non-selective β-adrenoceptor and $\alpha_1$-adrenoceptor antagonist.

2. The method of claim 1 wherein the compound is a compound of Formula I:

(I)

[Structure of carbazole with substituents $R_{13}, A, R_{12}, R_7, R_{11}, R_8, R_{10}, R_9$ and NH]

wherein:

$R_7$–$R_{13}$ are independently —H or —OH; and

A is a moiety of Formula II:

(II)

[Structure showing $R_3, R_6, O, X, Ar, R_2, R_5, OR_1, R_4$]

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —CH$_2$—O—;
- X is a single bond, —CH$_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
- $R_5$ and $R_6$ together represent methylenedioxy; and pharmaceutically acceptable salts thereof.

3. The method of claim 1 wherein the compound is a compound of Formula III:

(III)

[Structure of carbazole linked to $O, OR_1, R_3, R_2, R_4, N, X, Ar, R_6, R_5$]

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —CH$_2$—O—;
- X is a valency bond, —CH$_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

4. The method according to claim 1 wherein said compound is carvedilol.

5. A method for inhibiting Fas-mediated apoptosis which comprises administering to a mammal in need thereof an effective amount of a compound which is a dual non-selective β-adrenoceptor and α$_1$-adrenoceptor antagonist.

6. The method of claim 5 wherein the compound is a compound of Formula I:

(I)

[Structure of carbazole with substituents $R_{13}, A, R_{12}, R_7, R_{11}, R_8, R_{10}, R_9$ and NH]

wherein:

$R_7$–$R_{13}$ are independently —H or —OH; and

A is a moiety of Formula II.

(II)

[Structure showing $R_3, R_6, O, X, Ar, R_2, R_5, OR_1, R_4$]

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —CH$_2$—O—;
- X is a single bond, —CH$_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromnine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

7. The method of claim 5 wherein the compound is a compound of Formula III.

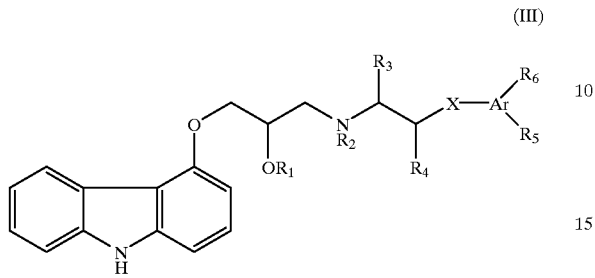

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

8. The method according to claim 5 wherein said compound is carvedilol.

9. A method for treating diseases wherein inhibition of Fas-mediated apoptosis is indicated which comprises administering to a mammal in need thereof an effective amount of a compound which is a dual non-selective β-adrenoceptor and $α_1$-adrenoceptor antagonist.

10. The method of claim 9 wherein the compound is a compound of Formula I:

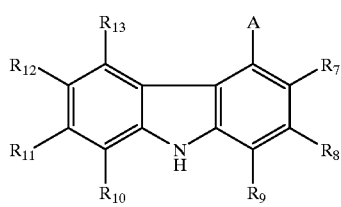

wherein:

$R_7$–$R_{13}$ are independently —H or —OH, and

A is a moiety of Formula II:

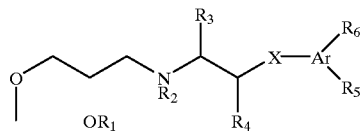

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a single bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

11. The method of claim 9 wherein the compound is a compound of Formula III:

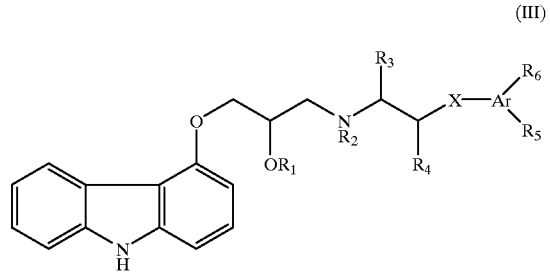

wherein:

$R_1$ is hydrogen, lower alkanoyl of up to 6 carbon atoms or aroyl selected from benzoyl and naphthoyl;

$R_2$ is hydrogen lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

12. The method according to claim 9 wherein said compound is carvedilol.

13. A method for blocking ischemia-induced apoptosis in cardiac cells which comprises administering to a mammal in need thereof an effective amount of a compound which is a dual non-selective β-adrenoceptor and $\alpha_1$-adrenoceptor antagonist.

14. The method of claim 13 wherein the compound is a compound of Formula I:

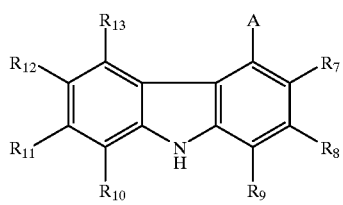

wherein:

$R_7$–$R_{13}$ are independently —H or —OH; and

A is a moiety of Formula II:

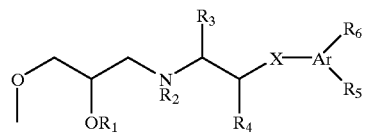

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a single bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

15. The method of claim 13 wherein the compound is a compound of Formula III.

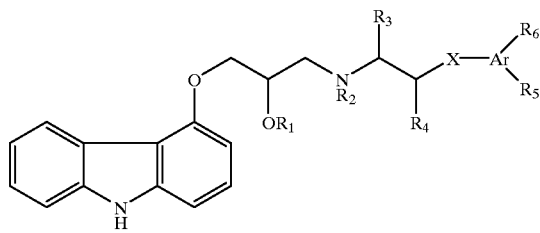

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a single bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

16. The method according to claim 13 wherein said compound is carvedilol.

17. A method for preventing or inhibiting tissue remodeling, for treating autoimmune diseases, or for inhibiting tumor growth and metastasis which comprises administering to a mammal in need thereof an effective amount of a compound which is a dual non-selective β-adrenoceptor and $\alpha_1$-adrenoceptor antagonist.

18. The method of claim 17 wherein the compound is a compound of Formula I:

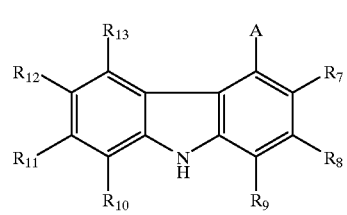

wherein:

$R_7$–$R_{13}$ are independently —H or —OH; and

A is a moiety of Formula II:

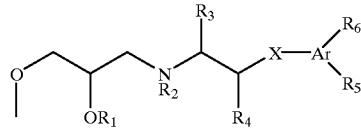

(II)

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —CH$_2$—O—;
- X is a single bond, —CH$_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms, or
- $R_5$ and $R_6$ together represent methylenedioxy;

and pharmaceutically acceptable salts thereof.

19. The method of claim 17 wherein the compound is a compound of Formula III:

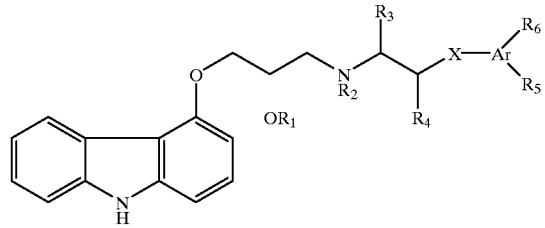

(III)

wherein:
- $R_1$ is hydrogen, lower alkanoyl of up to 6 carbon atoms or aroyl selected from benzoyl and naphthoyl;
- $R_2$ is hydrogen, lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —CH$_2$—O—;
- X is a valency bond, —CH$_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or or a pharmaceutically acceptable salt thereof.

20. The method according to claim 17 wherein said compound is carvedilol.

* * * * *